United States Patent [19]

Steffel

[11] Patent Number: 5,148,456
[45] Date of Patent: Sep. 15, 1992

[54] APPARATUS FOR TESTING WORKPIECES, IN PARTICULAR AUTOMOTIVE VEHICLE TIRES, BY MEANS OF X-RAYS

[76] Inventor: Horst Steffel, Am Fürstenhof 9, 2401 Gross Grönau, Fed. Rep. of Germany

[21] Appl. No.: 649,835

[22] Filed: Feb. 1, 1991

[30] Foreign Application Priority Data

Feb. 6, 1990 [DE] Fed. Rep. of Germany ......... 102379

[51] Int. Cl.$^5$ ............................................. G01B 15/06
[52] U.S. Cl. ....................................... 378/61; 378/58; 250/370.09
[58] Field of Search .................. 378/61, 57, 53, 54, 378/55, 57, 58; 250/370.01, 370.09, 370.11

[56] References Cited

U.S. PATENT DOCUMENTS 3,916,200 10/1975 Sparks, Jr. et al. ............ 250/370.01
4,870,279 9/1989 Cueman et al. ................ 250/370.11

FOREIGN PATENT DOCUMENTS 0315099 10/1988 European Pat. Off. .

Primary Examiner—David P. Porta
Attorney, Agent, or Firm—Kinney & Lange

[57] ABSTRACT

An apparatus for testing workpieces by means of X-rays includes at least one linear array of X-ray sensitive diodes which are closely spaced from each other. This allows the attainment of a high resolution. When e.g. yarns to be tested extend in the same direction as the diode line and are spaced for distances smaller than the corresponding extent of the receiving surfaces of the diodes, an effective resolution is not possible. This is why a "screen" is associated with the diode line, the screen having an aperture of a width which is smaller than the extent of the receiving surface transversely to the "screen" slot. Furthermore switch means allow skipping of certain diodes during scanning in order to obtain a scanning speed increase.

8 Claims, 3 Drawing Sheets

APPARATUS FOR TESTING WORKPIECES, IN PARTICULAR AUTOMOTIVE VEHICLE TIRES, BY MEANS OF X-RAYS

BACKGROUND OF THE INVENTION

The present invention relates to an apparatus for testing workpieces, in particular automotive vehicle tires, by means of X-rays, as defined in the introductory portion of patent claim 1.

European patent application 0 315 099 discloses an apparatus for multi-lateral X-ray testing of automotive vehicle tires, wherein an omni-directional X-ray tube disposed in proximity to the interior of a tire is used to transilluminate the side walls and tread of the tire. Outside of the tire to be tested there is provided a U-shaped assembly of three diode arrays receiving the X-rays from the tire. Each diode array comprises a linear line of light-sensitive diodes which are spaced from each other for 0.45 mm or even 0.225 mm. The receiving surfaces of the diodes are covered by a fluorescent layer. The light generated by the X-rays in the fluorescent layer is detected by the light-sensitive diode providing an electrical signal in response thereto. The diodes of the diode arrays are scanned by a scanner, and the output signals of the diode are transmitted to a store. An image reproducing device comprising a plurality of individual picture elements serves to generate image lines for each scanning sequence. Accordingly a predetermined surface portion of the tire to be tested is reproduced on the image screen of the diode arrays. The apparatus known from the European application enables a substantially vertical transillumination of all areas to be tested and thus a distortion-free reproduction on the reproduction apparatus. The diode arrays are adjustably mounted as to their spacing from the tire so that a uniform reproduction scale may be obtained for different tire sizes, which substantially facilitates testing of a tire by an operator. Of further advantage is that a screen reproduction is possible even with tire enforcements of plastic material (plastic cord) despite its poor contrast characteristics.

The light sensitive diodes including their electronic circuitry are received in a hermetically sealed housing so as to protect the sensitive elements from environmental disturbances, in particular dust. While the housing requires a through-slot for the X-rays, this through-slot is closed by an X-ray transmissive material so as to avoid absorption of the X-rays. Furthermore the housing area on both sides of the through-slot are provided with a lead-shield which is intended to prevent the X-rays penetrating through the housing walls from affecting or even destroying the electronic circuitry of the diodes.

In the prior art apparatus the dimension of the housing along the axis of radiation is relatively substantial, with the diodes being positioned adjacent the housing wall opposite the through-slot. The width of the through-slot cannot be made extremely small due to the fact that the incident radiation is to extend in the plane of the diode line. Manufacturing tolerances of the housing and of the other testing apparatus, accordingly require a minimum width of the through-slot. As a result thereof there is a certain risk that the areas adjacent to the diodes are also hit by X-rays, and sensitive parts an components may be detrimentally affected, and their life time will be substantially reduced. Furthermore the X-rays penetrating the housing across a substantial width may cause scattered radiation in the housing resulting also in a reduction of the life time of the electronic components.

By using small spacings of the diodes of a diode line a high resolution may be obtained so that e.g. tire re-enforcements of plastic fibres may be tested. In the art diode lines having a spacing of 0.2225 mm are known. The extent of the receiving surface of such diodes transverse to the diode line, however, is substantially greater for technical reasons and is presently about 0.6 mm. If a textile is to be tested wherein the fibres extend substantially parallel to the diode line and are spaced from each other for a distance that is smaller than the extent of the diode transverse to the diode line, there is a certain risk that a pair of fibres is simultaneously reproduced on the receiving surface An electric average value will result therefrom, and a proper resolution is not ensured any longer.

X-ray testing of e.g. automotive vehicle tires has been based on the fact that the tire basic material and the tire re-enforcements have different absorbing characteristics with respect to X-rays. So it is possible to obtain a relatively rich contrast between the tire basic material and e.g. steel re-enforcements. Furthermore it has become known to use textile re-enforcements (plastic cord) in tires, in particular in the tire side walls. Such re-enforcements have a reduced density as compared to rubber and provide only a relatively poor contrast. This is why tires including both steel and textile re-enforcements may not be tested in a single testing step. In order to obtain a sufficiently high resolution with respect to plastic cord, the X-ray tube must be operated at a relatively low voltage. This voltage would not be sufficient to make visible the structure of steel reenforcements. So it would be necessary to use different voltages depending on which type of tire re-enforcements are to be tested.

SUMMARY OF THE INVENTION

In the apparatus of the present invention a shield of X-ray absorbing material, e.g. lead, is disposed within the housing adjacent the diode line. Such shield provides a second through-slot aligned to the first through-slot and to the diode line and having a width which is smaller than that of the first through-slot and smaller than the extent of the diodes transversely to the diode line. In a preferred embodiment of invention the width of the second through-slot is almost half as large as the extent of the receiving surface of the diodes transversely to the diode line.

According to the present invention the first through-slot has been dimensioned so that a sufficient amount of X-rays enters the housing irrespective of any manufacturing tolerances. A second shield comprising a pair of lead strips or plates defines a smaller slot ensuring that it is only the receiving surface of the diodes and not any adjacent electronic circuitry that is impinged on by X-rays. The above dimensioning of the entry-slot provides the specific advantage that the X-rays impinge only on a portion of the receiving surface of the diode. This allows to obtain an increased resolution, with the degree of resolution depending on the width of the slot. If e.g. an automotive vehicle tire or a carcass-rod for making an automotive vehicle tire of the type which has yarns extending parallel to the length of the through-slot, the yarns may be arranged closely adjacent and yet can be made clearly visible.

In the apparatus of the present invention the diodes of the diode arrays are spaced so as to obtain a high resolution in order to make sufficiently visible in particular textile tire re-enforcements. The spacing of the diodes, in particular of the diode lines associated with the tire side walls will be dimensioned so as to obtain a sufficient resolution for plastic cord provided the voltage of the X-ray tube has been selected accordingly. The spacing is e.g. less than 0.3 mm or even smaller. In connection with conventional image reproducing devices this would mean a number of 1.024 or 2.048 diodes for each diode line. In particular the latter number of diodes per line is sufficient to obtain an acceptable resolution for plastic re-enforcements when the voltage of the X-ray tube has been selected properly.

For a pre-determined scanning frequency the duration of a scanning cycle depends on the number of scanned diodes per diode line. So the advantage of an increased resolution will have to be paid for by an increase of testing duration. Since the proportion of tires including plastic cord is small as compared to tires including exclusively steel re-enforcements, a system adapted for testing both plastic and steel cord tires would involve a relatively long testing duration per tire. In view of this problem a further aspect of the invention provides switching means for having the scanner selectively scan only each second, third etc. diode of a diode line. So the apparatus of the present invention in view of the structure of the diode line will be adapted to obtain a sufficient resolution for testing of plastic cord tires. If e.g. such a high resolution is not necessary for testing steel cord, the scanner is operated to scan not all diodes of a diode line but only each second, third etc. diode. This allows to reduce the scanning duration for a half, for a third, etc. The present invention allows to obtain an optimum testing duration depending on the type of re-enforcements of the tires to be tested. It is to be noted that the scanning of the diode lines may be performed in groups or batches rather than in series. During operation in the reduced resolution mode only a portion of the diodes of one group or batch will be scanned, e.g. pre-determined diodes (e.g. the even-numbered diodes of a row) will be skipped.

BRIEF DESCRIPTION OF THE DRAWINGS

A preferred embodiment of the present invention will be described with reference to the accompanying drawings.

DETAILED DESCRIPTION OF THE PREFERRED EMBODIMENTS

Figure 1:
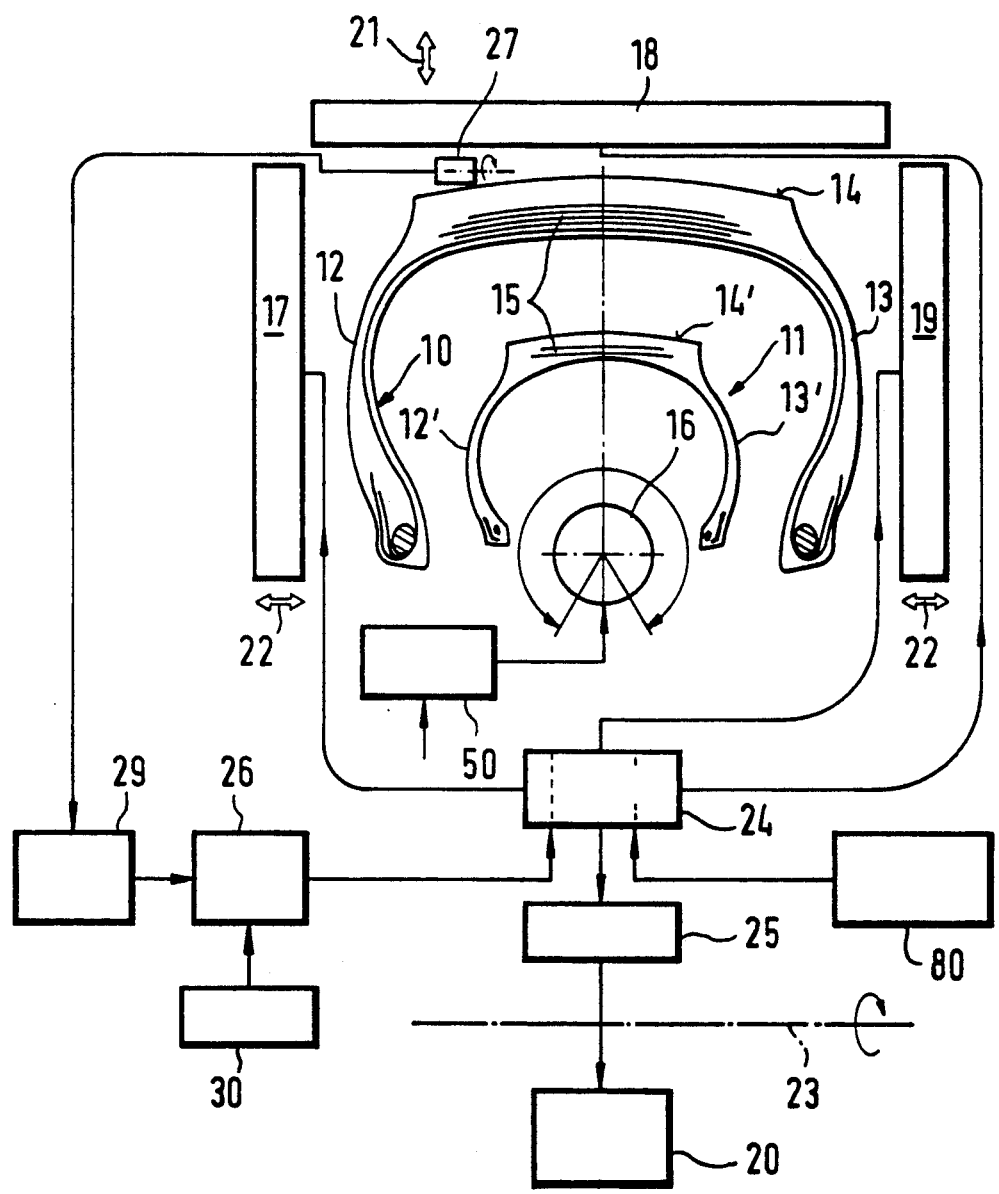
FIG. 1 shows, in a very schematic manner, the circuitry of a testing apparatus according to the present invention.

In FIG. 1 a pair of tires 10 and 11 of different sizes is shown. Their treads 14 and 14' include steel cord. Side walls 12, 13 and 12', 13' include either steel cord or plastic cord depending on the specific type of tire. Tire 10 or 11 is supported in a manner known per se for rotation about its axis. Rotating means (not shown) are used to rotate the tire about its axis 23 which may extend in a vertical plane; the circumferential speed of the tire may be set and adjusted by an operator. The structural means necessary to this end are not shown because they are well known to any person skilled in the art. Also the protection provisions commonly used in X-ray testing apparatus are not shown.

As may be seen in FIG. 1 an omni-directional X-ray tube 16 is located adjacent to the open side of tire 10 or 11, respectively. In a radial plane relative to the tire (which is identical to the drawing plane) the omni-directional X-ray tube 16 has a radiation angle of about 300°. Accordingly all portions of the tire in such radial plane will be transilluminated by X-ray tube 16, with the angle of penetration of the X-rays being approximately 90°. It is to be understood that the position of X-ray tube 16 could be varied, e.g. the X-ray tube 16 could be displaced towards or away from the interior of the tire. In a plane perpendicular to the radial plane X-ray tube 16 has a radiation angle of approximately 40°.

Diode arrays 17, 18, 19 are located on the outside of side walls 12, 13 and 12', 13', respectively, and on the outside of tread 14 or 14' respectively. The diode arrays are shown in FIG. 1 only diagrammatically. Each diode array 17, 18, 19 comprises a linear array of individual light sensitive diodes, e.g. 2048 diodes in each array and being spaced with respect to each other for 0.225 mm. The receiving surfaces of the diodes are provided with fluorescent layers transforming the X-rays into light suited to be detected by the diodes. The diode arrays or lines extend substantially parallel to the axis of tire 10, 11. The diodes are cyclically scanned by a scanner 24. The scanning signals in a manner known per se are stored in a storage 25 so that a row of scans appears simultaneously on a reproduction device 20, e.g. an image screen. Reproduction device 20 is shown also diagrammatically. It comprises three individual image screens (not shown).

The scanning speed of scanner 24 is controlled by a timer 26. A speed sensor 27, e.g. a tachometer roll is associated with tread 14, 14' of tire 10, 11. The output signal is transmitted to a control device 29 which is connected to timer 26. The scanning speed of scanner 24 is varied in accordance with the speed of tire 10, 11 in order to obtain a uniform reproduction scale for predetermined spacings of diode arrays 17, 18, 19 from the tire. Control device 29 calculates a mean value for the speed of the tire side walls. The scanning speed for the tread on the one hand and the scanning speed for the side walls 12, 12' on the other hand are quite different. If the spacing of diode arrays 17 to 19 from tire 10, 11 is changed, the scanning frequency also has to be changed. This is indicated by block 30.

As indicated by double arrows 21 and 22, the positioning of diode arrays 17 to 19 relative to tire 11, 12 may be varied. This will not be described any further and has become known e.g. from European patent application 0 315 099 mentioned above, the disclosure of which is incorporated by reference.

A voltage supply is indicated in the drawings by block 50. The voltage may be varied to provide for an optimum contrast. Plastic cord requires a "softer" voltage than steel cord. Furthermore the voltage depends on the thickness of the material to be tested. To this end block 50 may be connected to means receiving signals from a thickness measuring device.

The diodes of diode lines 17 to 19 are disposed closely adjacent to each other. Their spacing may be e.g. 0.225 mm. It is to be understood that the screen of monitor 20 will have a corresponding number of picture elements per line. The scanning speed is relatively high, preferably 1 pixel per millisecond.

A switching means 80 is associated with scanner 24. Switching means 80 may be used to vary the number of diodes to be scanned in each diode line. For example scanner 24 may be set so that it scans only each second diode of a diode line of diode arrays 17 to 19. Of course a scanning mode where only each second, third, etc. diode is scanned will result in a decreased resolution as compared to a scanning mode where each diode is being scanned; however the poorer resolution under certain circumstances will be sufficient to safely detect e.g. steel re-enforcements. When textile reenforcements are to be tested, switching means 80 is operated so that all diodes of a diode line are cyclically scanned.

While most of the tires have treads including steel re-enforcements, some tires to be tested have side walls including plastic re-enforcements. In view thereof it would be possible to have diode arrays 18 associated with the tread to include a smaller number of diodes, e.g. 1024, which all are scanned at each scanning cycle. In this case only diode arrays 17 and 19 associated with the tire side walls would include 2048 diodes, the scanning arrangement of which would be selected in accordance with the type of material to be tested.

Figure 2:
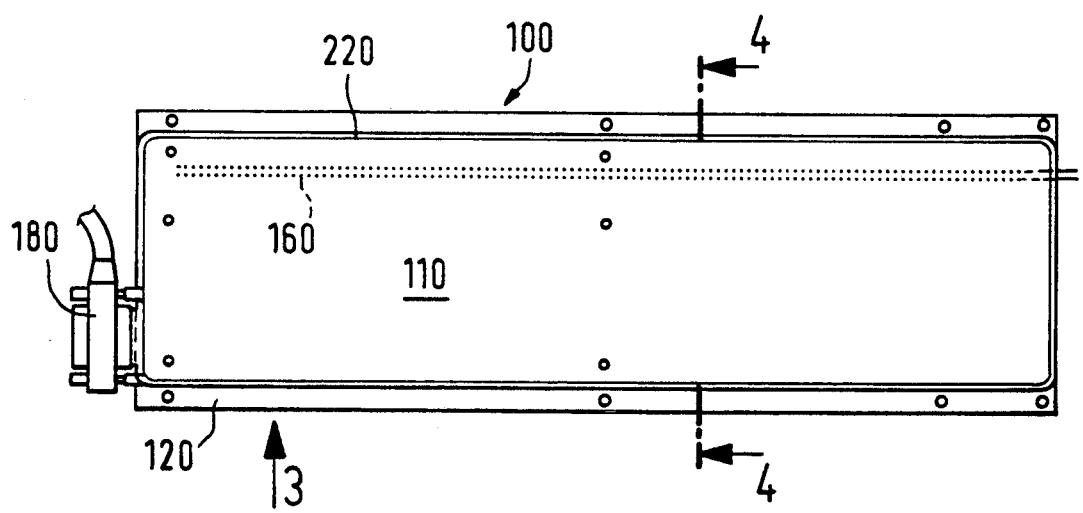
FIG. 2 is a top view of a diode array.
Figure 3:
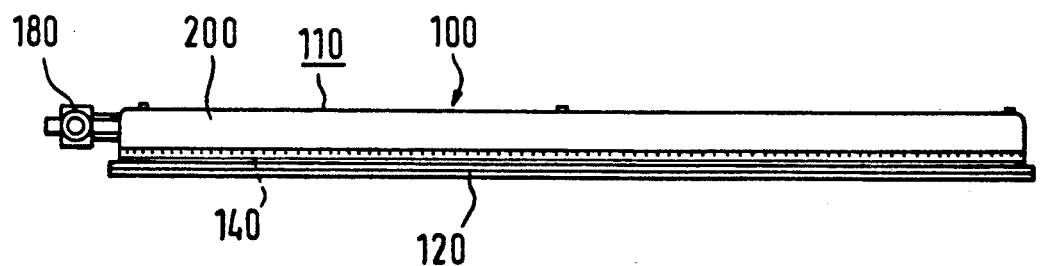
FIG. 3 is a side view of the diode array in FIG. 2 as viewed in the direction of arrow 3.

FIGS. 2 and 3 show a housing 100 having a relatively flat cap 110 and a plate 120 mounted to cap 110. Cap 110 has at its one front face an elongated through-slot 140 (FIG. 3) which is closed by a transmissive cover (not shown). A line of diodes 160 in housing 100 is located closely adjacent to the housing front face including slot 140. For example there are provided 1024 or 2048 diodes in one line, with the spacing of the diodes being 0.45 or 0.225 mm. At one end of housing 100 there are provided connection means 180 for the electrical supply of the diodes and signal feed lines to diodes 160 and connecting means for an electronic circuitry (not shown) of diodes 160 located within housing 100.

Figure 4:
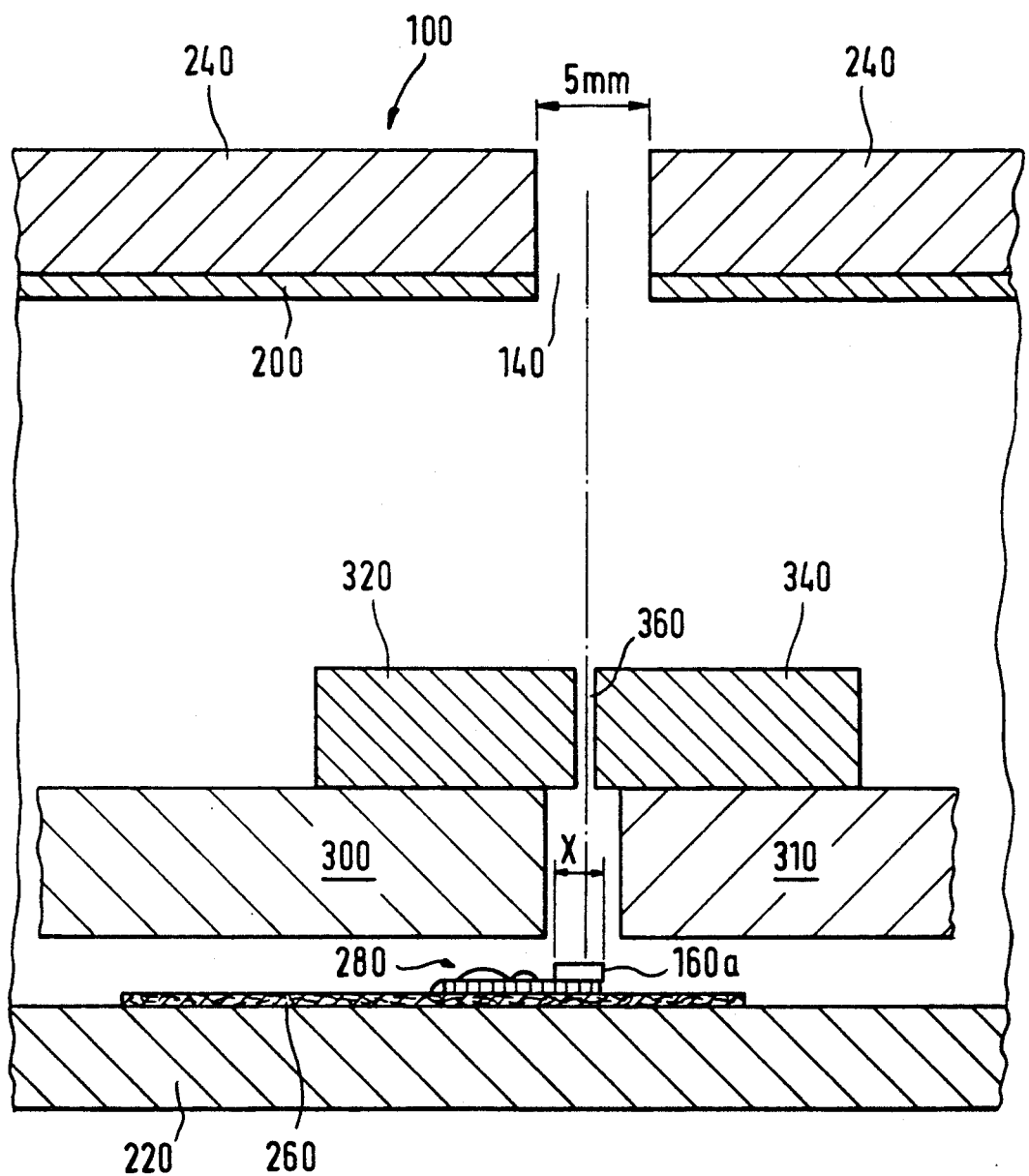
FIG. 4 is a cross section of the diode array along line 4—4 in FIG. 2.

In FIG. 4 a front wall 200 including through-slot 140 and an opposite back wall 220 are shown. A lead shield 240 terminating at through-slot 140 is mounted to front wall 200. The total through-slot defined thereby is of a width of approximately 5 mm. Through-slot 140 is normally closed by a cover (not shown) for preventing ingress of dust.

A printed card 260 is disposed at the inner side of opposite wall 220, the printed card carrying an electronic circuitry 280 for the diodes of which one is shown at 160a. Adjacent the electronic circuitry 280 and diodes 160a there are provided holders 300 and 310 of aluminum for holding narrow lead strips 320, 340. Strips 320, 340 define between them a slot 360 having a center line aligned to the center of through-slot 140. The common axis of slots 140, 360 is aligned to the axis of diode 160a. As shown in FIG. 4 holders 300, 310 are offset relative to slot 360. This prevents the occurrence of scattered radiation through holders 300, 310, which scattered radiation otherwise might detrimentally affect the electronic circuitry. The width of slot 360 is e.g. 0.2 to 0.4 mm. It is in any case smaller than the extent of the receiving surface X of diode 160a transversely to the longitudinal direction of slot 360 which is e.g. 0.6 mm.

The lead shield comprising strips or plates 320, 340 furthermore ensures that X-rays do not impinge on electronic circuitry 280, while diodes 160a receive a sufficient amount of X-rays due to the sufficient width of through-slot 140 despite of variations of the positioning of housing 100 relative to the X-ray source resulting from manufacturing tolerances.

Slot 360 could be provided in a single plate by a suitable machining method, e.g. by a laser process.

What is claimed is:

1. Apparatus for testing a workpiece by means of x-rays, wherein at least a linear array of x-ray sensitive diode and associated electronics is located in a hermetically sealed elongated housing including an elongated first through-slot extending parallel to the diode array and covered by an x-ray transmissive material, and a scanning means is provided for scanning the diodes at a predetermined variable frequency in order to store the output signals of the diodes and to reproduce them by monitoring means, with one scanning line for each scanning sequence being generated on the monitoring means, characterized in that the diodes are spaced from each other so as to obtain a high resolution and to make visible re-enforcements in the workpiece, the spacing distance being 0.5 mm or less, and in that a shield of x-ray absorbing material is located within the housing closely adjacent to the diode array, said shield defining a second through-slot aligned to said first through-slot and to said diode array, said second through-slot having a width smaller than that of said first through-slot and smaller than the extent (X) of the receiving surfaces of the diodes in a direction transversely to the diode array so as to improve the resolution of the array and to protect the electronic circuitry.

2. Apparatus according to claim 1 characterized in that the width of said second through-slot is almost half as large as said extent (X) of the receiving surfaces of the diodes.

3. Apparatus according to claim 1 characterized in that the width of said first through-slot exceeds the extent (X) of the receiving surfaces of the diodes.

4. Apparatus according to claim 1 characterized in that strips or plates of lead are mounted in the housing by a pair of holding means, the spacing of said holding means in the area of said second through-slot exceeding the width of said second through-slot.

5. Apparatus according to claim 1, wherein the workpiece is a automotive vehicle tire which is rotated wile being tested characterized in that switch means are associated with said scanning means so that said scanning means may selectively scan only each second, third, etc. diode at a predetermined scanning frequency in a scanning sequence.

6. Apparatus according to claim 1 characterized in that the spacing of the diodes if 0.3 mm or less.

7. Apparatus according to claim 5 wherein each at least one diode array is associated with an own scanning means, characterized in that said switch means is associated with the diode array.

8. Apparatus according to claim 5 characterized in that the scanning speed is at least 10 m/sec.

* * * * *